United States Patent [19]
Oren et al.

[11] Patent Number: 6,102,925
[45] Date of Patent: Aug. 15, 2000

[54] SURGICAL INSTRUMENTS FOR OPERATING ON JOINTS

[75] Inventors: Ran Oren; Dan Moor, both of Gaaton, Israel

[73] Assignee: T.A.G. Medical Products Ltd., Kibbutz Gaaton, Israel

[21] Appl. No.: 09/126,382

[22] Filed: Jul. 30, 1998

[51] Int. Cl.[7] .................................................. A61B 17/32
[52] U.S. Cl. .......................................... 606/170; 606/171
[58] Field of Search ..................................... 606/167, 170, 606/171, 175, 174, 207

[56] References Cited

U.S. PATENT DOCUMENTS

| | | |
|---|---|---|
| 4,444,184 | 4/1984 | Oretorp . |
| 4,662,371 | 5/1987 | Whipple et al. . |
| 5,254,129 | 10/1993 | Alexander . |
| 5,374,268 | 12/1994 | Sander . |
| 5,385,570 | 1/1995 | Chin et al. . |
| 5,443,474 | 8/1995 | Sfakianos et al. . |
| 5,443,475 | 8/1995 | Auerbach et al. . |
| 5,531,756 | 7/1996 | Larose . |
| 5,549,623 | 8/1996 | Sharpe et al. . |
| 5,582,618 | 12/1996 | Chin et al. . |
| 5,681,337 | 10/1997 | Bray, Jr. ................................. 606/171 |
| 5,704,925 | 1/1998 | Otten et al. ............................. 606/207 |

*Primary Examiner*—Michael Buiz
*Assistant Examiner*—Vy Q. Bui
*Attorney, Agent, or Firm*—Mark M. Friedman

[57] ABSTRACT

A grasper-cutter instrument for a resecting procedure including (a) an elongated shaft; (b) a stationary jaw connected at a distal end of the elongated shaft; (c) a rotating jaw connected at the distal end of the elongated shaft; (d) a grasp-release mechanism for rotating the rotating jaw in relation to the shaft and the stationary jaw to thereby actuate grasp and release relations of the stationary and rotating jaws; (e) a translating blade extending along a side of the shaft, the blade having a blade end and being translatable from a retracted position to an extended position in which the blade end is extended substantially up to distal ends of the stationary and rotating jaws; and (f) a retracting-extending mechanism for translating the blade from its retracted position to its extended position, and back.

A hook-cutter instrument for dissecting procedures including (a) an elongated shaft, the elongated shaft being formed with a guiding groove for engaging a translating blade; (b) a fenestrated hook being formed at a distal end of the elongated shaft; (c) a translating blade having a blade end extending along the shaft being engaged in, and translatable along, the guiding groove from a retracted position to an extended position in which the blade end is extended substantially up to a distal end of the fenestrated hook; and (d) a retracting extending mechanism for translating the blade from its retracted position to its extended position, and back.

9 Claims, 6 Drawing Sheets

SURGICAL INSTRUMENTS FOR OPERATING ON JOINTS

FIELD AND BACKGROUND OF THE INVENTION

The present invention relates to surgical instruments for operating on joints and, more particularly, to novel hook-cutter and grasper-cutter for arthroscopic endodissections and to a method of repairing meniscus injuries using these and/or other cutters.

Many surgical operations, for example, arthroscopic procedures and the like, require the surgeon to resect (i.e., cut and remove) small pieces of tissue from the body of the patient. Even though these pieces may be very tiny, it may be important that they not be dropped or otherwise mislaid, so as to remain within the body cavity after the operation.

For example, even small pieces of tissue can cause significant discomfort and pain if left within the interstices of human joints, where they may interfere with the healing and proper functioning of the joint, perhaps even causing further deterioration thereof. Alternatively, the procedure may involve a biopsy, wherein retaining the small piece may be critical for further diagnosis and treatment.

Furthermore, it is often important to accomplish surgical procedures in as quick, efficient and reliable a manner as is possible. Delay or error can result in complicating or serious consequences. While clamping the tissue with a pair of forceps (surgical pliers, graspers) and thereafter amputating it with a scalpel or the like may be crudely effective, this involves two separate instruments and a cumbersome and time-consuming series of operations. In some cases, there may not be enough room for both instruments, for example, within the interior of a human or animal joint.

Surgical instruments which save time and which free the hands of the surgeon for other functions can be of great aid in achieving successful surgery.

Under these guidelines, U.S. Pat. No. 5,254,129 to Alexander teaches a grasper-cutter, referred to therein as a resector. The resector instrument of Alexander has a set of opposed jaws that pivot about a common axis with respect to a shaft of the instrument's handle. The upper jaw has an upper blade rigidly affixed to one side thereof. A lower blade is rigidly affixed to the shaft. When the upper jaw and upper blade are jointly forced to pivot downward by a push rod on the shaft, the rotating upper blade moves past the stationary lower blade to amputate a piece of tissue in scissors-cutting fashion. The lower jaw is simultaneously forced (by the interposed tissue) to rotate about its pivot downwardly, i.e., in the same direction as and in fixed tandem with the upper jaw. The lower jaw is held tightly against the interposed tissue via a stiff spring against which the lower jaw is biased. The spring causes the jaws to tightly clasp the tissue in plier-clamping fashion during and after its amputation from its attachment. The instrument is operated by a scissors handle arrangement.

The instrument by Alexander suffers several limitations which, as is further detailed hereinunder, are addressed by the grasper-cutter of the present invention.

First, the blades of the instrument by Alexander are arranged and operated in a fashion similar to scissors. As such, at any given time point, the blades contact and act on a lengthy part of the dissected tissue, which requires greeter amount of force as compared with, for example, an instrument having blades designed to operate at a singular tissue point at a time.

Second, the jaws operating spring mechanism disclosed by Alexander is highly prone to being stuck and inoperative due to tissue debris which can accumulate within the mechanism. In this case both the cutting and the grasping functions are eliminated.

Third, since the operation of the jaws and the blades depend on the spring mechanism, cutting and grasping using the instrument by Alexander are progressed simultaneously. This design does not ensure positive grasping before cutting. As a result, in some cases, cutting may be completed prior to full grasping, which may lead to a loss of the dissected tissue part within the cavity of the organ or body part under operation.

Related art is further disclosed in U.S. Pat. Nos. 5,443,575, and 5,531,756, both teach cutters but fail to teach a grasper combined therewith, and U.S. Pat. No. 4,662,371, which teaches a grasper, yet fails to teach a cutter combined therewith.

U.S. Pat. No. 5,549,623 to Sharpe et al., and U.S. Pat. Nos. 5,385,570 and 5,582,618 to Chin et al., all teach hook-cutters, which are referred to therein as surgical cutting instruments. These instruments featuring a surgeon operable control handle for advancing a blade over a fenestrated hook so that tissue within said fenestrated window area is dissected. In both cases, the blade is translatable along a side of the hook. The limitation of these instrument is in the relation between the hook and the blade. Since the blade translates along one side of the hook, it is likely that tissue debris will stuck between the blade and the hook, to thereby separate the blade from the side of the hook and render the blade inoperative.

Related art is further disclosed in U.S. Pat. No. 4,444,184, which teaches a cutter yet fails to teach a hook; and U.S. Pat. No. 4,443,474, which teaches a hook, yet fails to teach a cutter.

Figure 1:
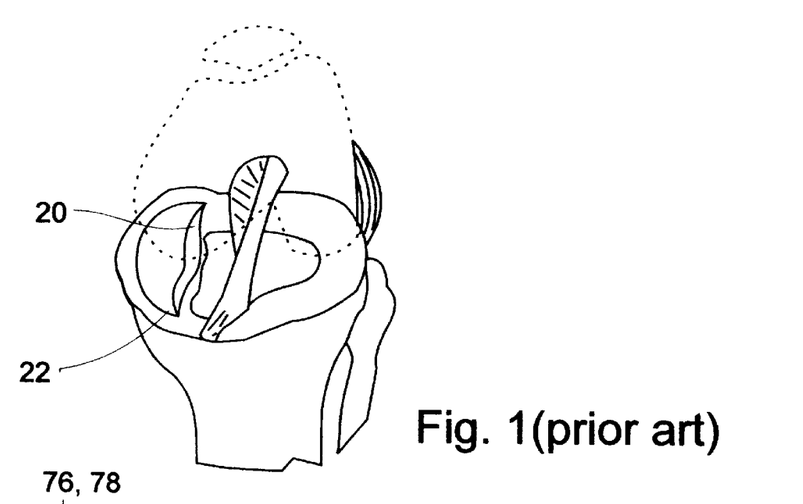
FIG. 1 in a schematic depiction of a bucket handle tear in a meniscus of a knee used to demonstrate a prior art method of repairing such a tear in the meniscus.

FIG. 1 describes steps undertaken during a prior art knee surgery, while repairing a "bucket handle" tear injury of the meniscus. Thus, in order to remove the tear, while holding the handle with a surgical grasper, a partial cut is first made in the posterior end of the torn tissue, as is indicated by arrow 20, such that a narrow posterior link connects the torn tissue to the posterior end of the meniscus. Then, a complete cut is made in the anterior end of the torn tissue, as is indicated by arrow 22, to thereby dissociate that end from the anterior part of the meniscus. Thereafter, the anterior free end of the torn tissue is grasped with the surgical grasper, and while twisting the grasper and therefore the torn tissue, the torn tissue is detached from the meniscus at the posterior link and is removed from the knee cavity.

This prior art method suffers two major limitations. First it calls for three portals to be formed in the knee of the patient, i.e., a portal for the cutter, a portal for the grasper and a third portal for an arthroscope which is used for lighting, imaging, washing and application of suction at the knee cavity. Second the procedure is lengthy, because each tool is used to perform a single action, i.e., the cutter only cuts and therefore the surgeon is in need for a grasper to be present and simultaneously operated. In addition, the cutter and grasper need to be relocated for each of the posterior and anterior cuts described above.

There is thus a widely recognized need for, and it would be highly advantageous to have, hook-cutter and grasper-cutter devoid of the above limitations associated with prior art equivalent instruments, which are used, according to the present invention, for repairing meniscus injuries, such as a bucket handle tear injury faster while restricting the number of portals formed in the operated knee to two portals.

SUMMARY OF THE INVENTION

Thus, according to one aspect of the present invention there is provided a grasper-cutter instrument for a resecting procedure comprising (a) an elongated shaft having a distal end and a proximal end; (b) a stationary jaw being stationary connected at, or integrally formed with, the distal end of the elongated shaft; (c) a rotating jaw being rotatably connected at the distal end of the elongated shaft, such that the stationary and rotating jaws can acquire grasp and release relations; (d) a grasp-release mechanism for rotating the rotating jaw in relation to the shaft and the stationary jaw, to thereby actuate the grasp and release relations of the stationary and rotating jaws; (e) a translating blade extending along a side of the shaft, the blade having a blade end and being translatable from a retracted position in which the blade end is regressed to an extended position in which the blade end is extended to a position closer to or substantially equals with distal ends of the stationary and rotating jaws; and (f) a retracting-extending mechanism for translating the blade from its retracted position to its extended position, and back.

According to further features in preferred embodiments of the invention described below, the grasper-cutter further comprising a jaws lock for locking the grasp-release mechanism when the stationary and rotating jaws are in a desired relation with respect to one another, e.g., in a grasp relation.

According to still further features in the described preferred embodiments the grasp-release mechanism includes (a) a stationary handle stationary connected to, or integrally formed with, the proximal end of the shaft; (b) a rotating handle rotatably connected to the stationary handle in a scissors-like fashion; and (c) an elongated linking mechanism, extending along and within the elongated shaft, the elongated linking mechanism is connected at one end thereof to the rotating handle and at another end thereof to the rotating jaw, such that rotating the rotating handle with respect to the stationary handle results in actuating the grasp and release relations of the stationary and rotating jaws.

According to still further features in the described preferred embodiments the retracting-extending mechanism includes a lever rotatable in relation to the stationary handle and connected at one end thereof to a translatable pin, the translatable pin is engaged in a housing formed in the stationary handle, the translatable pin is connected to the blade, such that when the lever is rotated with respect to the stationary handle, the translatable pin and therefore the blade both translate.

According to still further features in the described preferred embodiments the grasper-cutter instrument further comprising a stopping mechanism for limiting a force applied onto the stationary jaw by the rotating jaw when in the grasp relation.

According to still further features in the described preferred embodiments the grasper-cutter instrument further comprising a blade stabilizing mechanism being connected to the elongated shaft close to, or at the distal end thereof, the blade stabilizing mechanism being for holding the translating blade in intimate proximity with the elongated shaft and stationary and rotating jaws while translating, so as to prevent gap formation between the translating blade and the shaft or jaws.

According to another aspect of the present invention there is provided a hook-cutter instrument for dissecting procedures comprising (a) an elongated shaft having a distal end and a proximal end, the elongated shaft being formed with a guiding groove for engaging a translating blade; (b) a fenestrated hook being formed at the distal end of the elongated shaft; (c) a translating blade having a blade end and extending along the shaft being engaged in, and translatable along, the guiding groove from a retracted position, in which the blade end is regressed, to an extended position, in which the blade end is extended to a position closer to or substantially equals with a distal end of the fenestrated hook; and (d) a retracting-extending mechanism for translating the blade from its retracted position to its extended position and back.

According to still further features in the described preferred embodiments the hook-cutter instrument further comprising a handle being stationary connected at the proximal end to the elongated shaft.

According to still further features in the described preferred embodiments the retracting-extending mechanism is translatably engaged within a housing formed in the handle and is connected at a distal end thereof to the translating blade, such that translating the retracting-extending mechanism in relation to the handle results in translation of the translating blade.

According to yet another aspect of the present invention there is provided a method of removing a torn tissue of a bucket handle tear of a knee meniscus, the method comprising the steps of (a) inserting a hook-cutter into a knee cavity of the knee; (b) using the hook-cutter, forming a complete cut in one end of the torn tissue, so as to completely detach that end of the torn tissue from the meniscus; (c) inserting a grasper-cutter into the knee cavity of the knee; and (d) using the grasper-cutter, forming a complete cut in another end of the torn tissue, so as to completely detach the other end of the torn tissue from the meniscus, while grasping the torn tissue at that other end thereof.

According to still another aspect of the present invention there is provided a method of removing a torn tissue of a bucket handle tear of a knee meniscus, the method comprising the steps of (a) forming first and second portals in a knee; (b) through the first and second portals inserting an arthroscope and a hook-cutter into a knee cavity of the knee; (c) using the hook-cutter, forming a complete cut in one end of the torn tissue, so as to completely detach that end of the torn tissue from the meniscus; (d) removing the hook-cutter from the knee cavity; (e) through the first and second portals inserting the arthroscope and a grasper-cutter into the knee cavity of the knee; and (f) using the grasper-cutter, forming a complete cut in another end of the torn tissue, so as to completely detach the other end of the torn tissue from the meniscus, while grasping the torn tissue at that other end thereof.

According to still further features in the described preferred embodiments the method further comprising the steps of (g) while grasping the torn tissue, removing the grasper-cutter from the knee cavity; and (f) removing the arthroscope from the knee cavity.

The present invention successfully addresses the shortcomings of the presently known configurations by providing new surgical tools better adapted for faster and efficient joint repair procedures which overcome the limitations of the prior art.

BRIEF DESCRIPTION OF THE DRAWINGS

The invention herein described, by way of example only, with reference to the accompanying drawings, wherein.

DESCRIPTION OF THE PREFERRED EMBODIMENTS

The present invention is of surgical instruments which can be used for operating on joints. Specifically, the present invention provides novel hook-cutter and grasper-cutter which can be used for arthroscopic or other endodissections. In addition, the present invention is further of a novel knee repairing procedure, in which the novel hook-cutter and grasper-cutter or other hook-cutter and grasper-cutter are employed to treat, what is known in the art as a bucket handle tear of a meniscus.

The principles and operation of the instruments and method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring again to the drawings, FIGS. 2a–b and 3a–b illustrate a grasper-cutter instrument in accordance with the teachings of the present invention, which is referred to hereinbelow as grasper-cutter instrument 30, or instrument 30. Instrument 30 is adapted for resecting joint tissue, e.g., meniscus tissue. However, as will be appreciated by one ordinarily skilled in the art, grasper-cutter instrument 30 can be efficiently used for resecting any tissue in any organ, including, but not limited to, cancerous tissues.

Thus, grasper-cutter instrument 30 includes an elongated shaft 32, featuring a distal end 34 and a proximal end 36.

As used herein in the specification and in the claims section below, the terms "distal" and "proximal" refer to ends farther from and closer to the user, respectively.

Grasper-cutter instrument 30 further includes a stationary jaw 38. Jaw 38 is stationary connected at, or integrally formed with, distal end 34 of elongated shaft 32.

Grasper-cutter instrument 30 further includes a rotating jaw 40. Jaw 40 is rotatably connected at distal end 34 of elongated shaft 32 via a hinge 42, such that stationary 38 and rotating 40 jaws can acquire grasp and release relations. A grasp relation is specifically shown in FIGS. 2b and 3b, whereas a release relation is specifically shown in FIGS. 2a and 3a. Jaws 38 and/or 40 are preferably toothed, as is accepted in the art, so as to avoid tissue slippage from between the jaws when in the grasp relation.

Figure 2A:
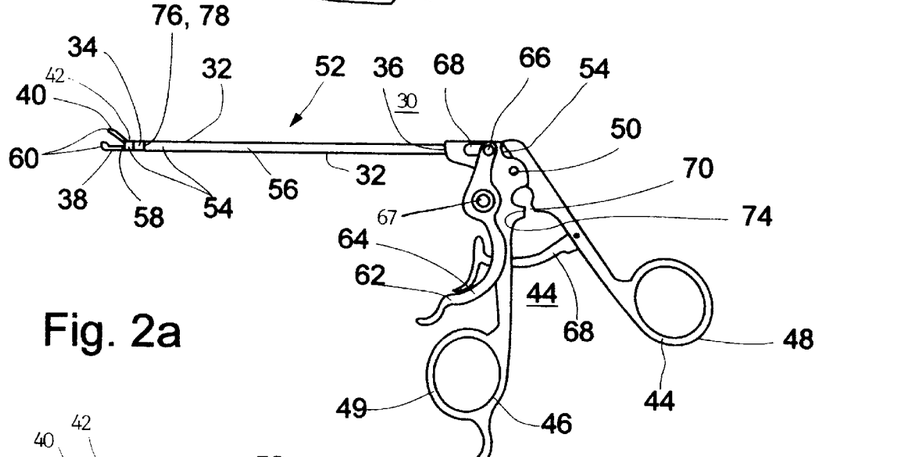
FIGS. 2a–b are side views of a grasper cutter according to the present invention is releasing and grasping positions, respectively.
Figure 2B:
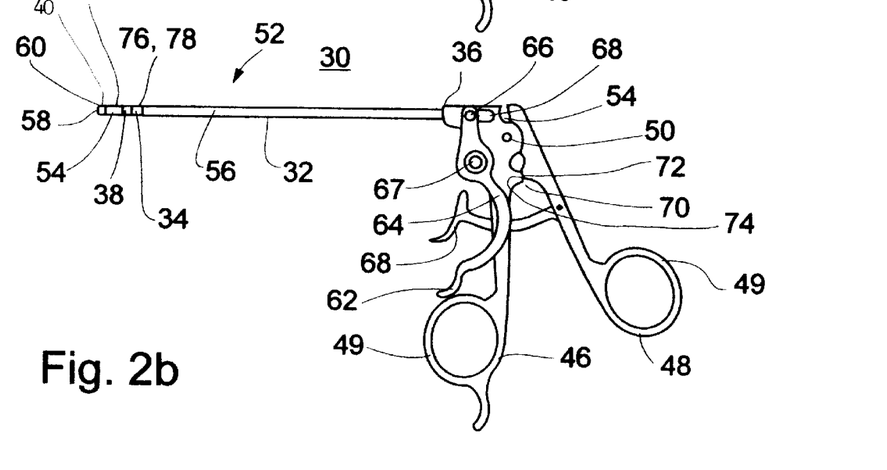
Figure 3A:
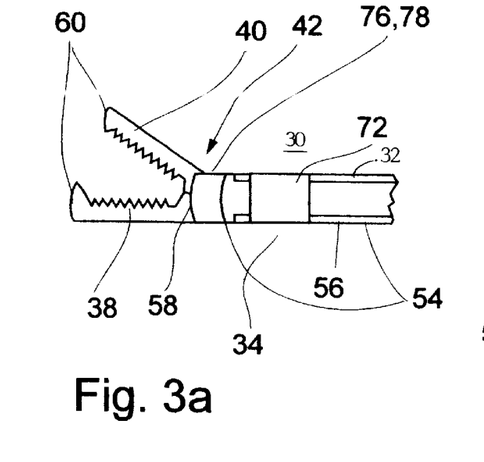
FIGS. 3a–b are enlarged side views of the distal portion of the grasper cutter according to the present invention, showing jaws thereof in a releasing position wherein a blade thereof is retracted (FIG. 3a), and jaws thereof in a grasping position wherein the blade thereof is extended (FIG. 3b)
Figure 3B:
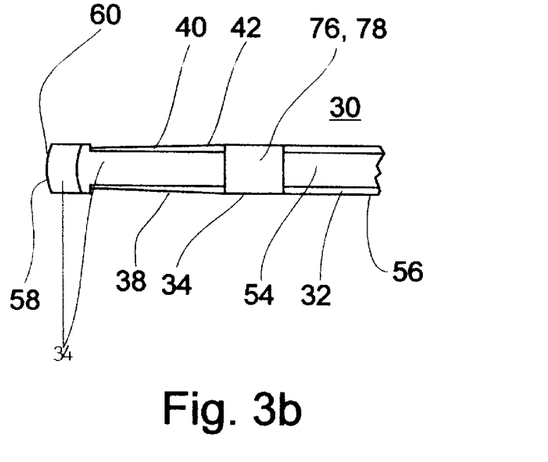

As shown in FIGS. 2a–b, grasper-cutter instrument 30 further includes a grasp-release mechanism 44. Mechanism 44 serves for rotating rotating jaw 40 in relation to shaft 32 and stationary jaw 38, to thereby actuate the grasp and release relations of stationary 38 and rotating 40 jaws.

According to a preferred embodiment of the present invention, grasp-release mechanism 44 includes a stationary handle 46. Handle 46 is stationary connected to, or integrally formed with, proximal end 36 of shaft 32, forming an angle therewith, preferably in a range of about 90 to about 120 degrees, a 90 degrees configuration is shown in FIGS. 2a–b.

Grasp-release mechanism 44 preferably further includes a rotating handle 48. Handle 48 is rotatably connected via a pivot 50 to stationary handle 46, in a scissors-like fashion. Handles 46 and 48 are preferably formed with fingers accepting rings 49.

Figure 7:
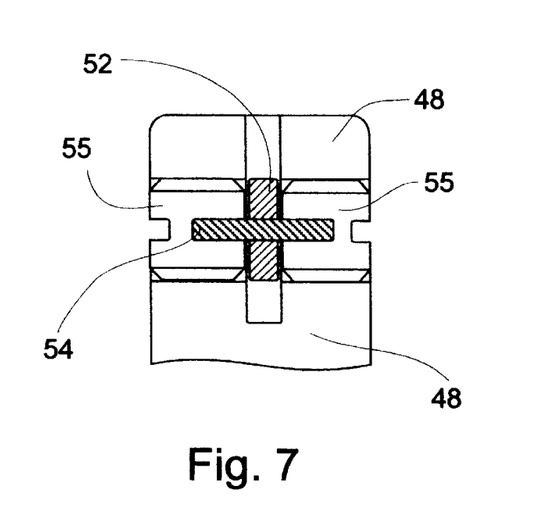
FIG. 7 is a cross sectional view of a proximal end of the grasper cutter according to the present invention, showing a shear pin implemented therein.

As shown in FIGS. 2a–b and 7, grasp-release mechanism 44 preferably further includes an elongated linking mechanism 52, extending along and within elongated shaft 32. Elongated linking mechanism 52 is connected at a proximal end thereof via a pivoting pin 54 engaged in a hosing 55 to rotating handle 48, and at a distal end thereof to rotating jaw 40, such that rotating rotating handle 48 with respect to stationary handle 46 results in actuating the grasp and release relations of stationary 38 and rotating jaws 40. In the configuration shown, bringing handle 48 closer to handle 46, results in stationary 38 and rotating jaws 40 acquiring the grasp relation (FIG. 2b), whereas removing handle 48 farther from handle 46, results in stationary 38 and rotating jaws 40 acquiring the release relation (FIG. 2a). Other configurations are envisaged.

Pivoting pin 54 is preferably a shear-pin designed to break under excessive load, thereby protecting against fracture of the components at the distal end of instrument 30.

According to a preferred embodiment of the present invention, grasper-cutter instrument 30 further includes a jaws lock 68. Lock 68 serves for locking grasp-release mechanism 44, when stationary 38 and rotating 40 jaws are in a desired relation, e.g., grasp relation. Lock 68 is preferably connected to, or integrally formed with, rotating handle 48 and locks onto stationary handle 46 via any locking mechanism accepted in the art.

As further shown in FIGS. 2a–b and 3a–b, grasper-cutter instrument 30 further includes a translating blade 54. Blade 54 extends along a side (left or right) 56 of shaft 32. Blade 54 is formed with a blade end 58 and is translatable from a retracted position (FIGS. 2a and 3a), in which blade end 58 is regressed, to an extended position (FIGS. 2b and 3b), in which blade end 58 is extended to a position closer to, or substantially equals with, distal ends 60 of stationary 38 and rotating 40 jaws. Blade 54 can, according to preferred embodiment of the invention, be disposable.

As further shown in FIGS. 2a–b, grasper-cutter instrument 30 further includes a retracting-extending mechanism 62. Mechanism 62 serves for translating blade 54 from its retracted position (FIG. 2a) to its extended position (FIG. 2b), and back.

Figure 8:
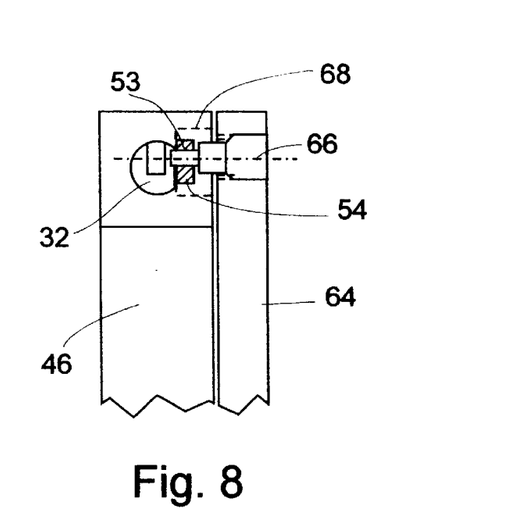
FIG. 8 is a cross sectional view in a proximal end of the grasper cutter according to the present invention, showing components of a retracting-extending mechanism implemented therein.

As shown in FIGS. 2a–b and 8, according to a preferred embodiment of the present invention, retracting-extending mechanism 62 includes a lever 64. Lever 64 is rotatable in relation to stationary handle 46 via a pivot 67, and it is connected at one end thereof to a translatable pin 66, which preferably forms an integral part thereof. Translatable pin 66 is engaged in a recess 68 formed in stationary handle 46 which allows pin 66 to fit into a 53 slot formed in blade 54, such that when lever 64 is rotated with respect to stationary handle 46, translatable pin 66 and therefore blade 54 both translate.

According to a preferred embodiment of the present invention, grasper-cutter instrument 30 further includes a stopping mechanism 70. Mechanism 70 serves for limiting a force applied onto stationary jaw 38 by rotating jaw 40 when in the grasp relation. Mechanism 70 preferably includes two stoppers 72 and 74, connected to, or integrally formed with, handles 48 and 46, respectively, such that stoppers 72 and 74 limit the minimal gap applicable between handles 48 and 46.

According to a preferred embodiment of the present invention, grasper-cutter instrument 30 further includes a blade stabilizing mechanism 76. Mechanism 76 is connected to elongated shaft 32 close to, or at, distal end 34 thereof. Blade stabilizing mechanism serves for holding translating blade 54 in intimate proximity with elongated shaft 32 and stationary 38 and rotating 40 jaws while translating, so as to prevent gap formation between translating blade 54 and shaft 32 or jaws 38 and 40. Blade stabilizing mechanism 76 preferably includes a supporting band 78.

The grasper-cutter described herein enjoys the following advantages with respect to the instrument disclosed in U.S. Pat. No. 5,254,129 to Alexander.

First, the single blade is arranged and operated in a fashion which concentrates all the sheering forces to a singular point, which requires less amount of force as compared with the prior art instrument.

Second, the jaws operating mechanism of the grasper-cutter according to the present invention is less prone to being stuck and inoperative due to tissue debris which can accumulate therein.

Third, cutting and grasping using the instrument of the present invention ensures that grasping precedes cutting, therefore, the risks of loosing the dissected tissue part are drastically reduced.

Referring now to FIGS. 4a–b and 5a–c, according to another aspect of the present invention there is provided a hook-cutter instrument, which is referred to hereinbelow as hook-cutter instrument 90, or instrument 90. Like instrument 30 described hereinabove, instrument 90 is adapted for dissecting joint tissue, e.g., meniscus tissue. However, as will be appreciated by one ordinarily skilled in the art, hook-cutter instrument 90 can be efficiently used for dissecting any tissue in any organ or body part, including, but not limited to, cancerous tissues.

Hook-cutter instrument 90 includes an elongated shaft 92 featuring a distal end 94 and a proximal end 96. Elongated shaft 92 is formed with a guiding groove 98, best seen in FIG. 5b, for engaging a translating blade, as further detailed hereinunder.

Hook-cutter instrument 90 further includes a fenestrated hook 100. Hook 100 is formed at distal end 94 of elongated shaft 92.

Hook-cutter instrument 90 further includes a translating blade 102. Blade 102 has a blade end 103, it extends along shaft 92 and it is engaged in, and translatable along, guiding groove 98 from a retracted position (shown in FIGS. 4a and 5a), in which blade end 103 is regressed, to an extended position (shown in FIGS. 4b and 5b–c), in which blade end 103 is extended to a position closer to or substantially equals with a distal end 106 of fenestrated hook 100.

Figure 4A:
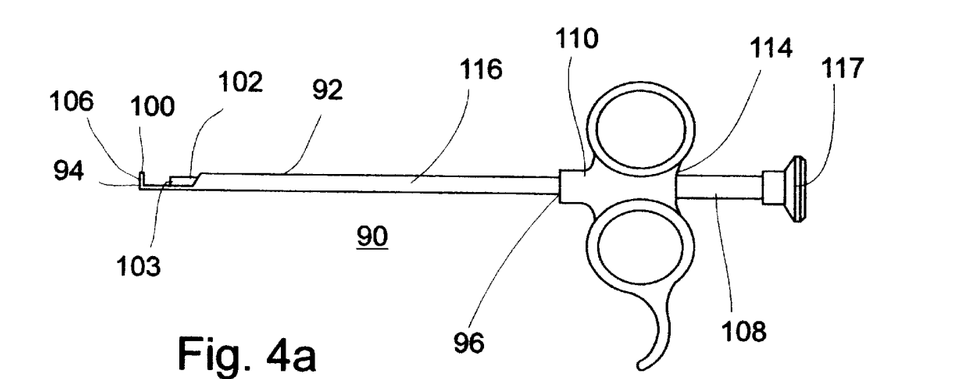
FIGS. 4a–b are side views of a hook-cutter according to the present invention, showing a blade thereof in retracted and extended positions, respectively.
Figure 4B:
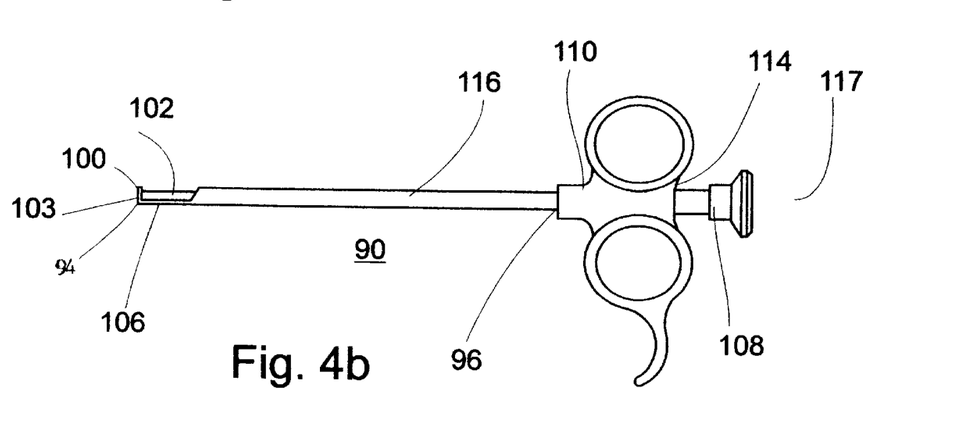
Figure 5A:
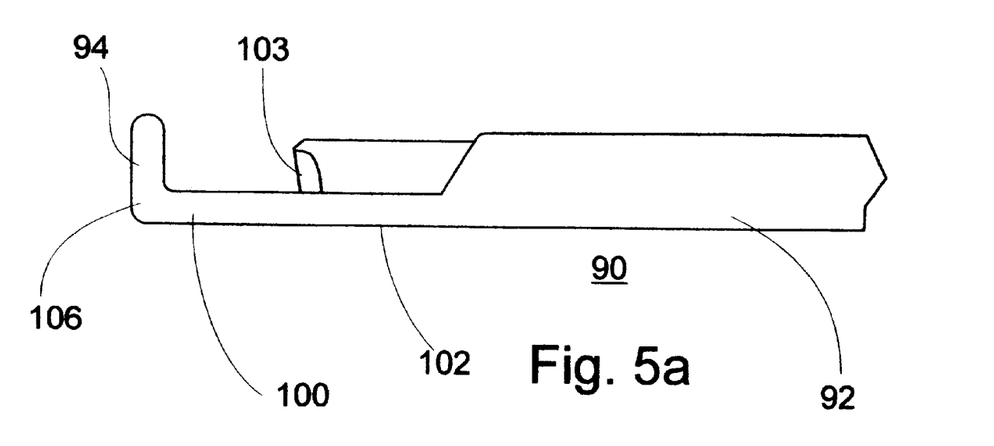
FIGS. 5a–c are enlarged side, top and frontal views of a distal end of the hook-cutter according to the present invention.
Figure 5B:
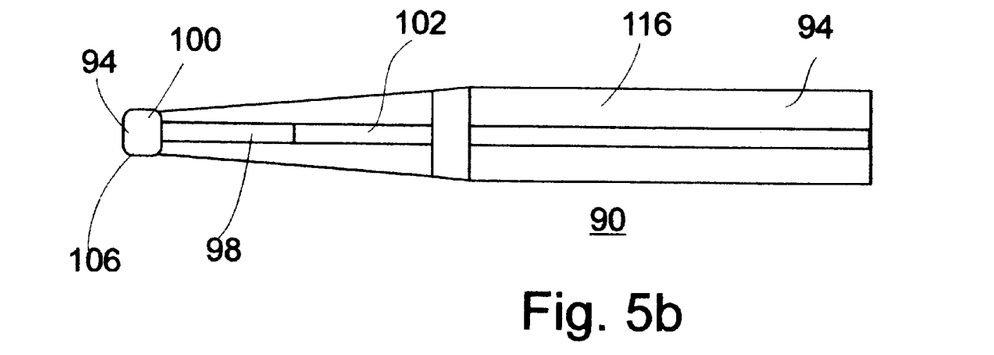
Figure 5C:
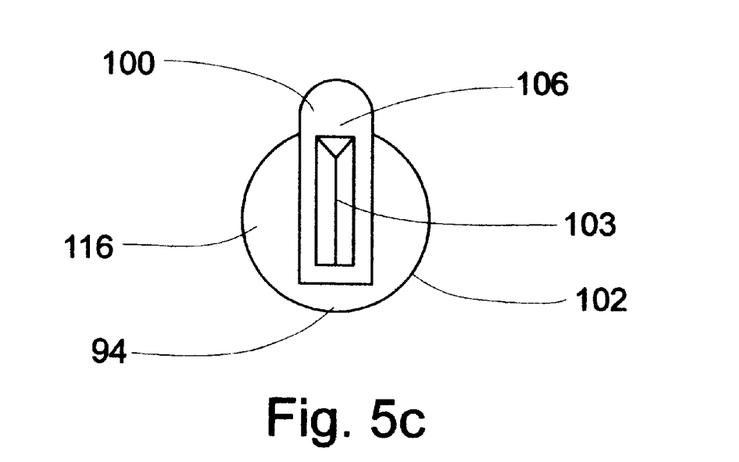
Figure 9:
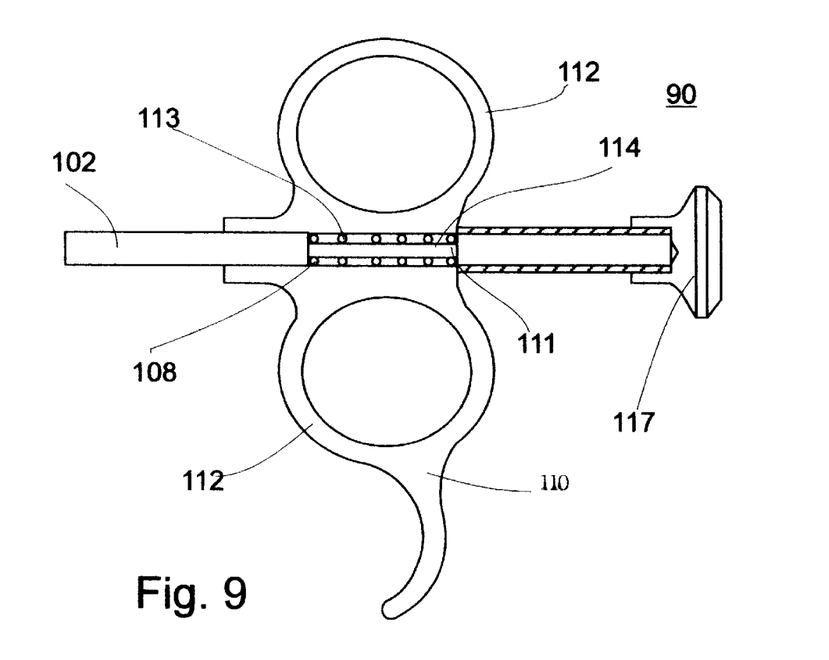
FIG. 9 is a cross sectional view in a proximal end of the hook-cutter according to the present invention, showing components of a retracting-extending mechanism implemented therein.

As further shown in FIGS. 4a–b and 9, hook-cutter instrument 90 further includes a retracting-extending mechanism 108. Mechanism 108 serves for translating blade from retracted position to position being closer to, or substantially equals with, distal end 106 of fenestrated hook.

According to a preferred embodiment of the present invention, hook-cutter instrument 90 further includes a handle 110. Handle 110 is stationary connected at proximal end 96 to elongated shaft 92. Handle 110 is preferably formed with fingers accepting rings 112.

According to a preferred embodiment of the present invention retracting-extending mechanism 108 is translatably engaged within a housing 114 formed in handle 110 and is connected at a distal end 111 thereof to translating blade 102, such that translating retracting-extending mechanism 108 via thumb knob 117 against a spring 113 in housing 114 in relation to handle 110 results in translation of translating blade 102.

Due to its design, the hook-cutter described herein in accordance with the present invention enjoys the following advantages with respect to the instruments disclosed in U.S. Pat. No. 5,549,623 to Sharpe et al. and 5,385,570 and 5,582,618 to Chin et al. While practicing with the prior art hook-cutters, in which the blade is translatable along a side of the hook, it is likely that tissue debris will stuck between the blade and the hook to separate the blade from the side of the hook and to thereby render the blade inoperative. In sharp distinction, according to the present invention the blade and hook are arranged on a single plane which eliminates this problem.

According to yet another aspect of the present invention there is provided a method of removing a torn tissue of a bucket handle tear of a knee meniscus. The method is effected by executing the following method steps, in which, in a first step, a hook-cutter is inserted into a knee cavity of the knee. The hook-cutter used is preferably the hook-cutter described hereinabove, however, other hook-cutters, for example, the hook-cutters described in U.S. Pat. No. 5,549,623 to Sharpe et al. and 5,385,570 and 5,582,618 to Chin et al., which are incorporated by reference as if fully set forth herein, can alternatively be employed.

In a second step of the method, the hook-cutter is used to form a complete cut in one end of the torn tissue of the bucket handle tear, so as to completely detach that end of the torn tissue from the meniscus. This cut is preferably performed in the posterior end of the torn tissue.

In a third step of the method, a grasper-cutter is inserted into the knee cavity of the knee. The grasper-cutter used is preferably the grasper-cutter described hereinabove, however, other grasper-cutters, for example, the grasper-cutter described in U.S. Pat. No. 5,254,129 to Alexander, which is incorporated by reference as if fully set forth herein, can alternatively be employed.

In a fourth step of the method, the grasper-cutter is used to form a second complete cut in the other end of the torn tissue, so as to completely detach the other end of the torn tissue from the meniscus, while grasping the torn tissue at that other end thereof. This cut is preferably performed in the anterior end of the torn tissue.

The torn tissue is thereafter removed from the knee cavity by means of the grasper-cutter.

With reference now to FIGS. 6a–d, schematically described are steps undertaken while implementing the method according to the present invention in removing a torn tissue 161 of a bucket tear handle in an injured meniscus 163 in a knee cavity 158 of a knee 154.

Figure 6A:
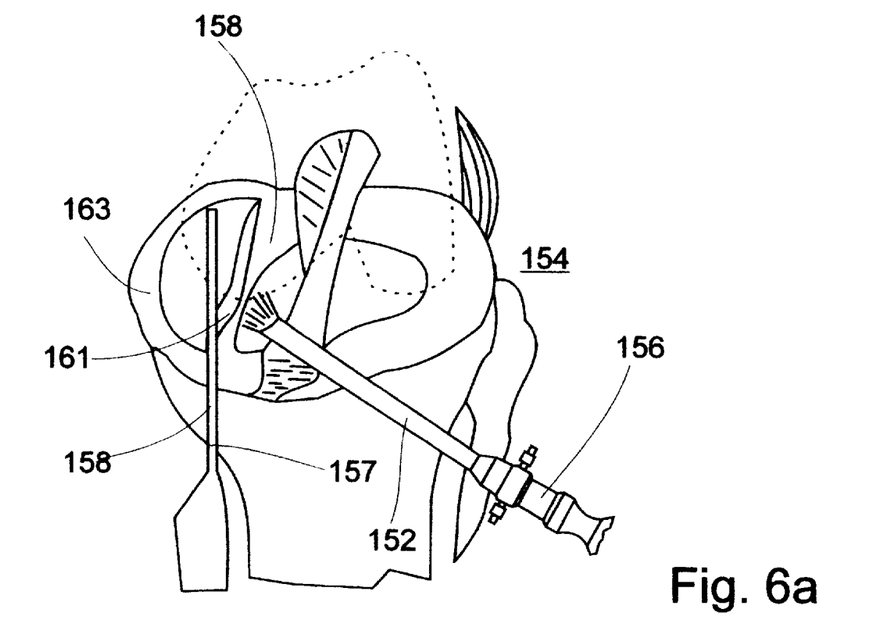
FIGS. 6a–d demonstrate several steps undertaken while repairing a bucket handle tear in a meniscus of a knee according to the method of the present invention.

Thus, in a first step of the method, first and second portals 150 and 152 are formed knee 154.

As shown in FIG. 6a, at a second step of the method, portals 150 and 152 serve for inserting a conventional surgical hook 157 and an arthroscope 156, respectively, into knee cavity 158.

As used herein in the specification and in the claims section below, the term "arthroscope" refers to an endoscope specialized for use in the diagnosis and surgical treatment of diseased or injured joints. Such an endoscope typically serves for illuminating, imaging, washing and applying suction in knee cavity 158. Such endoscopes are well known in the art and are therefore not further described herein.

Aided by arthroscope 156 and surgical hook 157 the surgeon evaluates the knee condition and arranges torn tissue 161 in a fashion to render it easier to remove, as is described in relation to the subsequent steps of the method.

Figure 6B:
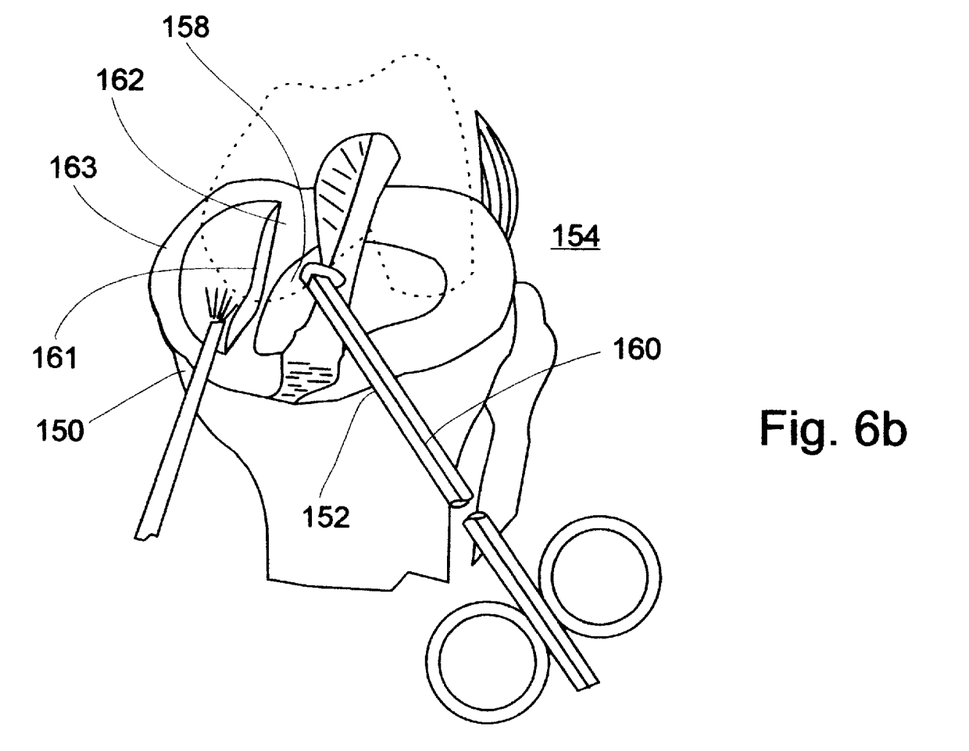

As shown in FIG. 6b, in a subsequent step of the method, the surgeon inserts arthroscope 156 and a hook-cutter 160 into knee cavity 158, through first 150 and second 152 holes, respectively. Using hook-cutter 160, the surgeon forms a complete cut in one end of torn tissue 161, typically the posterior end thereof 162, so as to completely detach that end 162 of torn tissue 161 from meniscus 163. Hook-cutter 160 and arthroscope 156 are thereafter removed from knee cavity 158.

Figure 6C:
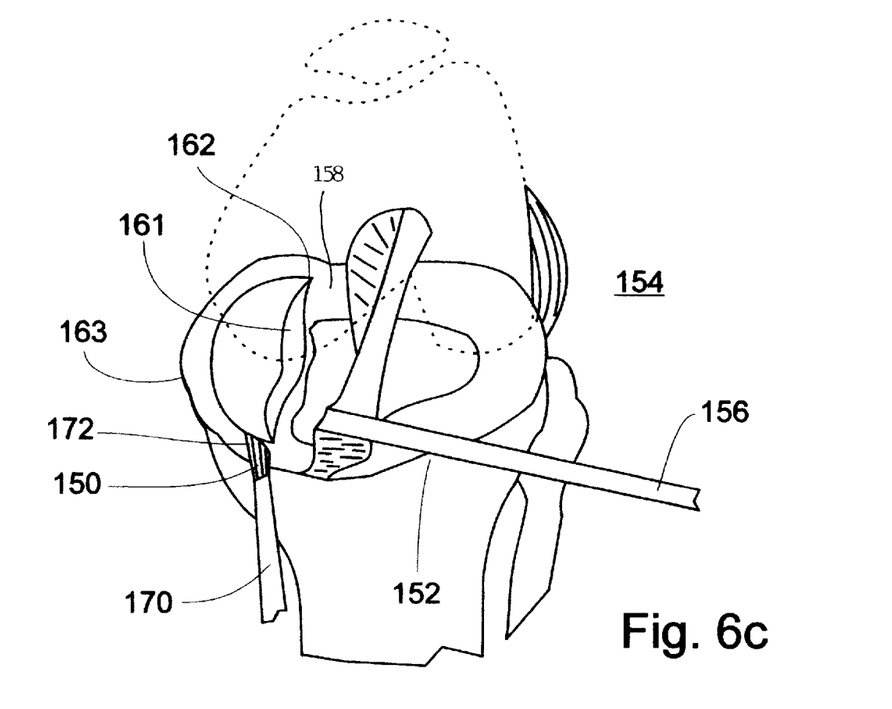

As shown in FIG. 6c, in a subsequent step of the method, the surgeon inserts a grasper-cutter 170 and reinserts arthroscope 156 into knee cavity 158, via portals 150 and 152, respectively. Using grasper-cutter 170, the surgeon forms a complete cut in the other end 172 of torn tissue 161, which is preferably its anterior end, so as to completely detach torn tissue 161 from meniscus 163, while grasping torn tissue 161 at end 172 thereof.

Figure 6D:
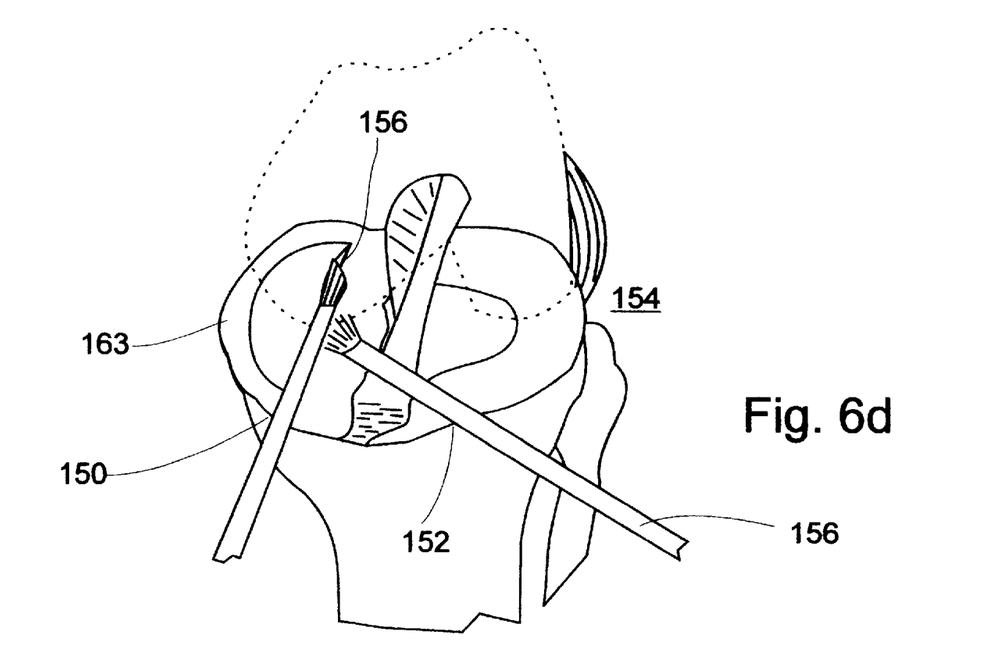

As shown in FIG. 6d, thereafter, while still grasping torn tissue 161, the surgeon removes grasper-cutter 170 from knee cavity 158. Thereafter arthroscope 156 is also removed from knee cavity 158. Then, portals 150 and 152 are stitched.

The method according to the present invention enjoys two major advantages as is compared with the prior art method described in the Background section hereinabove. First it requires only two, instead of three, portals to be formed in the knee of the patient, which ensures less damage to healthy knee tissue, less risk of infection and faster healing. Second, it is about 20 minutes faster to perform as compared with the prior art method.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A grasper-cutter instrument for a resecting procedure comprising:
   (a) an elongated shaft having a distal end and a proximal end;
   (b) a stationary jaw being stationary connected at, or integrally formed with, said distal end of said elongated shaft;
   (c) a rotating jaw being rotatably connected at said distal end of said elongated shaft, such that said stationary and rotating jaws can acquire grasp and release relations;
   (d) a grasp-release mechanism for rotating said rotating jaw in relation to said shaft and said stationary jaw to thereby actuate said grasp and release relations of said stationary and rotating jaws;
   (e) a translating blade extending along a side of said shaft, said blade having a blade end and being translatable from a retracted position in which said blade end is regressed to an extended position in which said blade end is extended to a position closer to or substantially equals with distal ends of said stationary and rotating jaws; and
   (f) a retracting-extending mechanism for translating said blade from said retracted position to said extended position and back.

2. The grasper-cutter instrument of claim 1, further comprising a jaws lock for locking said grasp-release mechanism when said stationary and rotating jaws are in a desired relation.

3. The grasper-cutter instrument of claim 1, wherein said grasp-release mechanism includes:
   (a) a stationary handle stationary connected to, or integrally formed with, said proximal end of said shaft;
   (b) a rotating handle rotatably connected to said stationary handle in a scissors-like fashion; and
   (c) an elongated linking mechanism, extending along and within said elongated shaft, said elongated linking mechanism is connected at one end thereof to said rotating handle and at another end thereof to said rotating jaw, such that rotating said rotating handle with respect to said stationary handle results in actuating said grasp and release relations of said stationary and rotating jaws.

4. The grasper-cutter instrument of claim 3, wherein said retracting-extending mechanism includes a lever rotatable in relation to said stationary handle and connected at one end thereof to a translatable pin, said translatable pin is engaged in a housing formed in said stationary handle, said translatable pin is connected to said blade, such that when said lever is rotated with respect to said stationary handle, said translatable pin and therefore said blade both translate.

5. The grasper-cutter instrument of claim 1, further comprising a stopping mechanism for limiting a force applied onto said stationary jaw by said rotating jaw when in said grasp relation.

6. The grasper-cutter instrument of claim 1, further comprising a blade stabilizing mechanism being connected to said elongated shaft close to or at said distal end thereof, said blade stabilizing mechanism being for holding said translating blade in intimate proximity with said elongated shaft and stationary and rotating jaws while translating, so as to prevent gap formation between said translating blade and said shaft or jaws.

7. A method of removing a torn tissue of a bucket handle tear of a knee meniscus, the method comprising the steps of:
   (a) forming first and second portals in a knee;
   (b) through said first and second portals inserting an arthroscope and a hook-cutter into a knee cavity of the knee;
   (c) using said hook-cutter, forming a complete cut in one end of the torn tissue, so as to completely detach that end of the torn tissue from the meniscus;

(d) removing said hook-cutter from the knee cavity;

(e) through said first and second portals inserting said arthroscope and a grasper-cutter into the knee cavity of the knee; and (f) using said grasper-cutter, forming a complete cut in another end of the torn tissue, so as to completely detach the other end of the torn tissue from the meniscus, while grasping the torn tissue at the other end thereof.

8. The method of claim 7, further comprising the steps of:

(g) while grasping the torn tissue, removing said grasper-cutter from the knee cavity; and (h) removing said arthroscope from the knee cavity.

9. A method of removing a torn tissue of a bucket handle tear of a knee meniscus, the method comprising the steps of:

(a) inserting a hook-cutter into a knee cavity of the knee;

(b) using said hook-cutter, forming a complete cut in one end of the torn tissue, so as to completely detach that end of the torn tissue from the meniscus;

(c) inserting a grasper-cutter into the knee cavity of the knee; and (d) using said grasper-cutter, forming a complete cut in another end of the torn tissue, so as to completely detach the other end of the torn tissue from the meniscus, while grasping the torn tissue at that other end thereof.

\* \* \* \* \*